(12) United States Patent
Lee et al.

(10) Patent No.: US 8,845,716 B2
(45) Date of Patent: Sep. 30, 2014

(54) MULTILAYER-COATED STENT FOR CONTROLLED DRUG RELEASE AND MANUFACTURING METHOD THEREOF

(75) Inventors: Kyung Bum Lee, Seoul (KR); Seung Jung Park, Seoul (KR); Cheol Whan Lee, Seoul (KR)

(73) Assignee: Kyung Bum Lee, Seoul (KR)

( * ) Notice: Subject to any disclaimer, the term of this patent is extended or adjusted under 35 U.S.C. 154(b) by 618 days.

(21) Appl. No.: 11/210,807

(22) Filed: Aug. 25, 2005

(65) Prior Publication Data

US 2006/0161242 A1    Jul. 20, 2006

(30) Foreign Application Priority Data

Jan. 17, 2005  (KR) .................... 10-2005-0004331

(51) Int. Cl.
*A61F 2/06*    (2013.01)
*A61L 31/16*   (2006.01)
*A61L 31/10*   (2006.01)

(52) U.S. Cl.
CPC .............. *A61L 31/16* (2013.01); *A61L 2300/61* (2013.01); *A61L 31/10* (2013.01); *A61L 2420/08* (2013.01)
USPC ........................................ 623/1.44; 623/1.42

(58) Field of Classification Search
USPC ........... 623/1.43, 1.42, 1.15, 1.13, 23.7, 1.39, 623/1.44, 1.46, 1.45; 427/2.25
See application file for complete search history.

(56) References Cited

U.S. PATENT DOCUMENTS

| | | | | |
|---|---|---|---|---|
| 4,491,648 A | * | 1/1985 | Durbin et al. | 525/89 |
| 5,370,682 A | * | 12/1994 | Schmitt | 623/1.52 |
| 5,824,048 A | * | 10/1998 | Tuch | 128/898 |
| 5,936,934 A | * | 8/1999 | Kuribayashi et al. | 369/286 |
| 6,174,329 B1 | * | 1/2001 | Callol et al. | 623/1.34 |
| 6,358,556 B1 | | 3/2002 | Ding et al. | |
| 6,541,678 B2 | * | 4/2003 | Klein | 602/41 |

(Continued)

FOREIGN PATENT DOCUMENTS

WO    WO 03/079936 A1    10/2003
WO    WO 03/099169 A1    12/2003

OTHER PUBLICATIONS

Tao P. et al: "Role of polymers in improving the results of stenting in coronary arteries" Biomaterials, Elsevier Science Publishers BV., Barking, GB, vol. 17, No. 7, 1996, pp. 685-694, XP004032760 ISSN: 0142-9612.

*Primary Examiner* — Thomas J Sweet
*Assistant Examiner* — Matthew Schall
(74) *Attorney, Agent, or Firm* — The PL Law Group, PLLC (57) ABSTRACT

The present invention provides a multilayer-coated stent for controlled drug release, comprising: a first base layer formed on a stent support and made of poly(ethylene-co-vinylacetate) or polystyrene-ethylene-butylene rubber polymer; a second coating layer formed on the first base layer and made of a biocompatible or a bioabsorbable polymer and a drug component; and a third coating layer formed on the second coating layer and made of a biocompatible or a bioabsorbable polymer and a drug component different from the drug component of the second coating layer. The inventive stent can deliver a broad range of therapeutic substances for a long time and prevent the early rapid release of the drug components in blood. Also, unlike the existing drug-coated stents, the inventive stent includes two kinds of drugs complementary to each other, but can optimize the efficacy of the drugs by differentiating the control of drug release according to time.

15 Claims, 4 Drawing Sheets

(56) References Cited

U.S. PATENT DOCUMENTS

| | | | |
|---|---|---|---|
| 6,626,936 B2 * | 9/2003 | Stinson | 623/1.15 |
| 6,699,280 B2 * | 3/2004 | Camrud et al. | 623/1.16 |
| 7,087,269 B2 * | 8/2006 | Lee et al. | 427/532 |
| 7,357,815 B2 * | 4/2008 | Shaoulian et al. | 623/2.36 |
| 7,473,417 B2 * | 1/2009 | Zeltinger et al. | 424/78.08 |
| 2002/0051730 A1 | 5/2002 | Bodnar et al. | |
| 2002/0094440 A1 | 7/2002 | Llanos et al. | |
| 2002/0190419 A1 * | 12/2002 | Albrecht et al. | 264/171.14 |
| 2003/0028243 A1 * | 2/2003 | Bates et al. | 623/1.15 |
| 2003/0149471 A1 * | 8/2003 | Briana et al. | 623/1.13 |
| 2003/0153901 A1 * | 8/2003 | Herweck et al. | 604/891.1 |
| 2003/0191528 A1 * | 10/2003 | Quijano et al. | 623/2.37 |
| 2004/0034407 A1 * | 2/2004 | Sherry | 623/1.15 |
| 2004/0051201 A1 * | 3/2004 | Greenhalgh et al. | 264/172.11 |
| 2004/0126405 A1 * | 7/2004 | Sahatjian et al. | 424/423 |
| 2004/0180131 A1 * | 9/2004 | Cheng | 427/2.24 |
| 2004/0204750 A1 * | 10/2004 | Dinh | 623/1.15 |
| 2004/0215313 A1 | 10/2004 | Cheng | |
| 2004/0230288 A1 * | 11/2004 | Rosenthal | 623/1.13 |
| 2004/0254634 A1 * | 12/2004 | Verlee et al. | 623/1.16 |
| 2005/0010279 A1 * | 1/2005 | Tenerz et al. | 623/1.16 |
| 2005/0070996 A1 * | 3/2005 | Dinh et al. | 623/1.42 |
| 2005/0107870 A1 * | 5/2005 | Wang et al. | 623/1.44 |
| 2005/0119723 A1 * | 6/2005 | Peacock, III | 623/1.15 |
| 2005/0158363 A1 * | 7/2005 | Shalaby | 424/426 |
| 2005/0172471 A1 * | 8/2005 | Vietmeier | 29/447 |
| 2005/0212630 A1 * | 9/2005 | Buckley et al. | 335/35 |
| 2005/0220842 A1 * | 10/2005 | DeWitt et al. | 424/423 |
| 2005/0222671 A1 * | 10/2005 | Schaeffer et al. | 623/1.15 |
| 2005/0278015 A1 * | 12/2005 | Dave et al. | 623/1.38 |
| 2005/0288782 A1 * | 12/2005 | Moaddeb et al. | 623/2.37 |
| 2006/0085062 A1 * | 4/2006 | Lee et al. | 623/1.39 |
| 2006/0121080 A1 * | 6/2006 | Lye et al. | 424/423 |
| 2006/0147491 A1 * | 7/2006 | DeWitt et al. | 424/426 |
| 2006/0193886 A1 * | 8/2006 | Owens et al. | 424/423 |
| 2006/0229711 A1 * | 10/2006 | Yan et al. | 623/1.38 |
| 2006/0235507 A1 * | 10/2006 | Brightbill | 623/1.42 |
| 2006/0241741 A1 * | 10/2006 | Lootz | 623/1.34 |
| 2007/0055368 A1 * | 3/2007 | Rhee et al. | 623/2.37 |
| 2007/0156230 A1 * | 7/2007 | Dugan et al. | 623/1.16 |
| 2007/0191708 A1 * | 8/2007 | Gerold et al. | 600/431 |
| 2008/0033531 A1 * | 2/2008 | Barthel et al. | 623/1.15 |
| 2008/0065200 A1 * | 3/2008 | Binyamin et al. | 623/1.35 |
| 2008/0102035 A1 * | 5/2008 | Dave et al. | 424/9.4 |
| 2008/0125852 A1 * | 5/2008 | Garrison et al. | 623/1.13 |
| 2008/0183285 A1 * | 7/2008 | Shaoulian et al. | 623/2.37 |
| 2008/0200981 A1 * | 8/2008 | Shaoulian et al. | 623/2.37 |
| 2008/0215129 A1 * | 9/2008 | Venturelli et al. | 623/1.11 |
| 2008/0215145 A1 * | 9/2008 | Moaddeb et al. | 623/2.37 |
| 2008/0243230 A1 * | 10/2008 | Lootz et al. | 623/1.15 |

\* cited by examiner

MULTILAYER-COATED STENT FOR CONTROLLED DRUG RELEASE AND MANUFACTURING METHOD THEREOF

FIELD OF THE INVENTION

The present invention relates to a cardiovascular stent and a manufacturing method thereof. More particularly, the present invention relates to a multilayer-coated stent for controlled drug release, which shows a reduction in restenosis resulting from neointimal proliferation, as well as a manufacturing method thereof.

BACKGROUND OF THE RELATED ART

Currently, stent devices for preventing restenosis by supplying a cardiovascular or luminal support or reinforcement are widely used, but they have a significant clinical problem of restenosis with rates ranging 20~40%. Mechanical intervention via stents have a low effect on the treatment of neointimal proliferation resulting from a complex immune response causing the enlargement and disruption of atherosclerotic plaques. This is because neointimal proliferation causes inflammation due to the initial enlargement and disruption of atherosclerotic lesions, so that a series of cellular events that activate an immune system are induced and cytokine that stimulates cell proliferation in the smooth muscle layer of the vessel media is released. This stimulation of cell proliferation can lead to coronary vessel restenosis.

In a recent attempt to cope with the problem of neointimal proliferation, drug-releasing stents coated with immune inhibitors or therapeutic agents are widely used. Immune inhibitors, such as rapamycin, prevent the initiation of DNA synthesis by targeting the G1-stage cells. Therapeutic agents, such as paclitaxel and other taxane derivatives, act on cells of the M-stage among stages known as the cell cycle, in the cellular DNA level, by preventing the dissolution of microtubules and interfering with cellular division. These strategies have significant advantages, but there are not only limitations in the duration of drug effect around the stents but also the risk of undesired systemic toxicity.

Accordingly, there is a need for an improved drug-coated stent which can mitigate the problem of early rapid release of drugs at the stent sites and improve the problem of limitations in therapeutic effects, which can be caused in the case of a single drug.

SUMMARY OF THE INVENTION

Therefore, the present invention has been made to solve the above-described problems occurring in the prior art, and it is an object of the present invention to provide a multilayer-coated stent for controlled drug release, which prevents the early rapid release of drug components in blood, is very excellent in performance for the control of drug release, and includes two kinds of drugs but can significantly reduce restenosis after implantation by effectively controlling the release period of each of the drugs, as well as a manufacturing method thereof.

To achieve the above object, in one aspect, the present invention provides a multilayer-coated stent for controlled drug release, which comprises: a first base layer formed on a stent support and made of a poly(ethylene-co-vinylacetate) or styrene rubber polymer; a second coating layer formed on the first base layer and made of a biocompatible polymer and a drug component; and a third coating layer formed on the second coating layer and made of a biocompatible polymer and a drug component different from the drug component of the second coating layer.

In another aspect, the present invention provide a method for manufacturing a multilayer-coated stent for controlled drug release, the method comprising the steps of: forming on a stent support a first base layer made of a poly(ethylene-co-vinylacetate) or styrene rubber polymer, by ultrasonic spraying followed by solvent evaporation; forming on the first base layer a second coating layer made of a biocompatible polymer and a first drug component; and forming on the second coating layer a third coating layer made of a biocompatible polymer and a drug component different from the drug component of the second coating layer.

DETAILED DESCRIPTION OF THE PREFERRED EMBODIMENT

Hereinafter, the present invention will be described in more detail.

Figure 1:
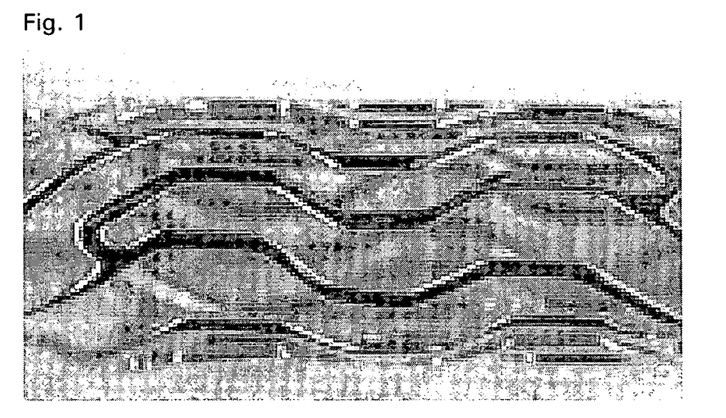
FIG. 1 is a perspective view showing a cardiovascular stent according to the present invention.

In a multilayer-coated stent for controlled drug release according to the present invention, the multilayer structure consists of a first base layer, a second coating layer and a third coating layer, as described below.

The first base layer is a coating layer made of a poly (ethylene-co-vinylacetate) or styrene rubber polymer which provides sufficient toughness or elasticity and metal adhesion.

The second coating layer is formed by coating a biocompatible polymer and a drug component on the base layer.

Examples of the biocompatible polymer contained in the second coating layer include, but are not limited to, polyvinyl alcohol, polyethylene glycol, polylactide, polyglycolide, polylactide copolymer, polyethylene oxide, polydioxanone, polycaprolactone, polyphosphagen, polyanhydride, polyamino acid, cellulose acetate butyrate, cellulose triacetate, polyacrylate, polyacrylamide, polyurethane, polysiloxane, polyvinylpyrrolidone (PVP), and copolymers thereof.

Examples of the drug component contained in the second coating layer include, but are not limited to, antiplatelet drugs including Cilostazol (chemical name: 6-[4-(1-cyclohexyl-1H-tetrazol-5-yl)butoxy]-3,4-dihydro-2(1H)-quinolinone; molecular formula: $C_{20}H_{27}N_5O_2$; and molecular weight: 369.47) represented by the following formula 1, antithrombotic agents, antiproliferative agents, growth factors, antioxidants, and radioactive compounds:

(Formula 1)

The drug component contained in the second coating layer is continuously released slowly over a long term while achieving therapeutic effects, such as platelet aggregation inhibition, vasodilation, the inhibition of vascular smooth muscle cells, and the reduction of serum thyroglobulin.

The third coating layer is formed by coating on the second coating layer a biocompatible polymer and a drug component different from the drug component of the second coating layer.

Examples of the biocompatible polymer contained in the third coating layer include, but are not limited to, polyvinyl alcohol, polyethylene glycol, polylactide, polyglycolide, polylactide copolymer, polyethylene oxide, polydioxanone, polycaprolactone, polyphosphagen, polyanhydride, polyamino acid, polyethylene-vinylacetate, cellulose acetate butyrate, cellulose triacetate, polyacrylate, polyacrylamide, polyurethane, polysiloxane, polyvinylpyrrolidone (PVP), and copolymers thereof, as exemplified for the biocompatible polymer which can be used in the second coating layer.

Examples of the drug component contained in the third coating layer include, but are not limited to, Taxol and its derivatives (e.g., Paclitaxel represented by the following formula 2 and having a molecular formula of $C_{47}H_{51}NO_{14}$, a molecular weight of 853.9 and a melting point of 213-216° C.), Colchicine, Lovastatin, Trapidyl, Hirudin, Ticlopidine, and growth factors, such as vascular endothelial growth factors (VEGF), transforming growth factor-beta (TGF-β), insulin-like growth factors (IGF), platelet-derived growth factors (PDGF) and fibroblast growth factors (FGF):

{Formula 2}

The drug component of the third coating layer acts to prevent the dissolution of microtubules and interfere with cellular division, thus inhibiting the growth of vascular endothelial cells.

To make a surface-coated stent, the present invention involves depositing a coating solution on a stent support by a dip coating or spray coating process. The spray coating process is preferably used. Particularly, the spray coating process including the use of an ultrasonic spray system is most preferably used.

The drop size of the ultrasonic spray coating solution is influenced by nozzle vibration frequency and the surface tension and density of an atomized solution. In this regard, the mean drop size is inversely proportional to ⅔ times the vibrational frequency. Also, the higher the vibrational frequency, the smaller the mean drop size. To maintain the multilayer-coated structure according to the present invention, the mean drop size is preferably in a range of 20-60 μm, and the flow rate is preferably in a range of 0.01-0.05 ml/min. If the mean drop size and the flow rate are out of the specified ranges, the atomized state of liquid drops will not be constant to cause a non-uniform coating surface.

Figure 2A:
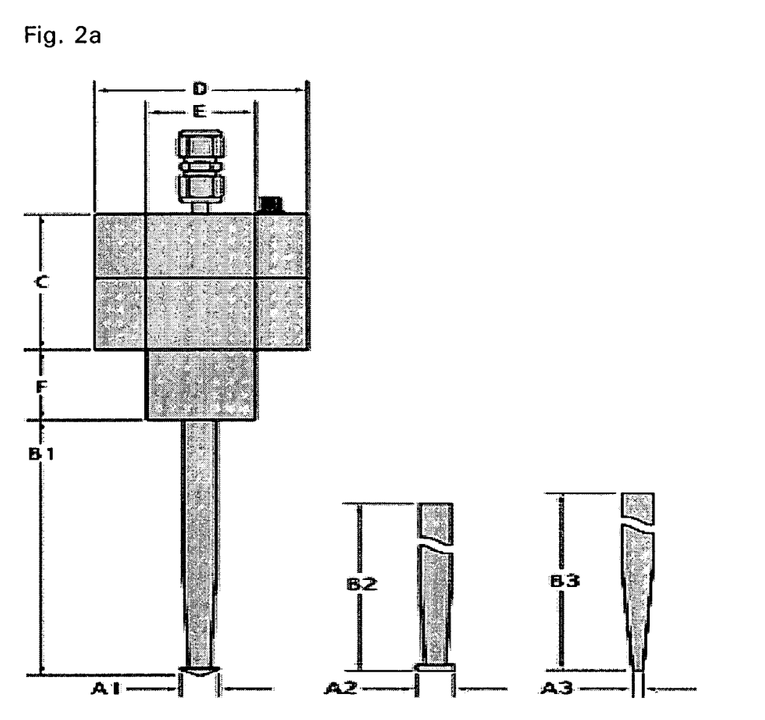
FIG. 2a is a drawing for explaining the dimensions of a spray nozzle used in the inventive ultrasonic spray system.

FIG. 2a is a drawing for explaining the dimensions of a spray nozzle, a core component of an ultrasonic spray system used in spray coating in Examples of the present invention as described later, and specific data for each of the dimensions are shown in Table 1 below.

TABLE 1

| A1 | B1 | A2 | B2 | A3 | B3 | C | D | E | F |
|---|---|---|---|---|---|---|---|---|---|
| 6.35 mm | 63.8 mm | 6.35 mm | 61.7 mm | 2.29 mm | 70.87 mm | 35.56 mm | 36.58 mm | 19.05 mm | 29.72 mm |

Figure 2B:
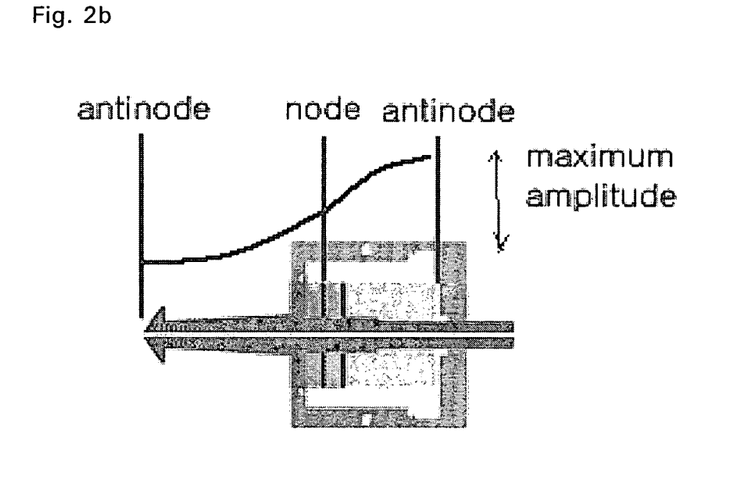
FIG. 2b shows the correlation between the length, wavelength and maximum vibration amplitude of an ultrasonic spray nozzle.

As shown in FIG. 2b, the nozzle is so designed that the node plane is located between crystals. In order to effectively achieve atomization using ultrasonic energy, the atomization surface (nozzle tip) should be located at an anti-node where the vibration amplitude becomes the maximum. For this purpose, the length of the nozzle should be a multiple of ½ wavelength. Since the wavelength is proportional to the vibrational frequency, the nozzle dimensions depend on the vibrational frequency.

If one surface of the stent support is to be coated, only the surface to be coated will be exposed to the dipping or spraying solution. The stent support may comprise a plurality of micropores or a porous material facilitating deposition or coating on the applicable surface of the stent support, in which the micropores preferably have a size of about less than 50 μm. If the size of the micropores is more than 50 μm, the drugs will be excessively released at an early stage or it will be difficult to control the drug release at a constant rate. In the multilayer-coated stent for controlled drug release according to the present invention, the stent support may be made of a biocompatible metal selected from the group consisting of stainless steel, cobalt-chrome alloy, tantalum, nitinol or gold.

Specifically, the method for manufacturing the multilayer-coated stent for controlled drug release according to the present invention comprises the following steps.

The first step is to treat the surface of the stent support. In this step, the stent support is washed with a mixed solvent of ethanol and distilled water to remove impurities from the entire surface of the stent support, and dried in a vacuum oven at 50-150° C. and less than 0.01 mTorr for 12-24 hours.

In the second step, a poly(ethylene-co-vinylacetate) or styrene rubber polymer is first coated on the stent support by solvent evaporation to form a first base layer.

In the third step, a second coating layer made of a first drug, such as a platelet aggregation inhibitor, and a biocompatible polymer, is formed on the first base layer.

Examples of the biocompatible polymer used in the step of forming the second coating layer include, but are not limited to, polyvinyl alcohol, polyethylene glycol, polylactide, polyglycolide, polylactide copolymer, polyethylene oxide, polydioxanone, polycaprolactone, polyphosphagen, polyanhydride, polyamino acid, polyethylene-vinylacetate, cellulose acetate butyrate, cellulose triacetate, polyacrylate, polyacrylamide, polyurethane, polysiloxane, polyvinylpyrrolidone (PVP), and copolymers thereof.

In the step of forming the second coating layer, the content of the biocompatible polymer in the second coating solution is preferably in a range of 3-30% (w/v), and the weight ratio between the biocompatible polymer and the drug in the second coating solution is preferably in a range of 1:1-10:1. If the polymer content and the weight ratio between the polymer and the drug are out of the specified ranges, a constant coating layer can not be formed or the polymer layer can be compact, thus making the drug release difficult. Examples of the drug component include, but are not limited to, antiplatelet drugs including Cilostazol, antioxidants including Probucol, antithrombotic agents, antiproliferative agents, growth factors and radioactive compounds.

In the fourth step, a third coating layer made of a second drug, such as paclitaxel, and a biocompatible polymer, is formed on the second coating layer.

Examples of the biocompatible polymer used in the step of forming the third coating layer include, but are not limited to, polyvinyl alcohol, polyethylene glycol, polylactide, polyglycolide, polylactide copolymer, polyethylene oxide, polydioxanone, polycaprolactone, polyphosphagen, polyanhydride, polyamino acid, polyethylene-vinylacetate, cellulose acetate butyrate, cellulose triacetate, polyacrylate, polyacrylamide, polyurethane, polysiloxane, polyvinylpyrrolidone (PVP), and copolymers thereof.

In the step of forming the third coating layer, the content of the polymer in the coating solution is preferably in a range of 5-25% (w/v), and the weight ratio between the biocompatible polymer and the drug is preferably in a range of 1:5-10:1. If the polymer content and the weight ratio between the polymer and the drug are out of the specified ranges, the non-uniformity of the coating layer can be caused and a constant release of the drug can become difficult. Examples of the drug in this step include, but are not limited to, Taxol and its derivatives, Colchicine, Lovastatin, Trapidyl, Hirudin, Ticlopidine, and growth factors, such as vascular endothelial growth factors (VEGF), transforming growth factor-beta (TGF-$\beta$), insulin-like growth factors (IGF), platelet-derived growth factors (PDGF) and fibroblast growth factors (FGF).

The stent coated by the above-described steps is continuously washed five times with distilled water for 5 minutes to 5 hours. After washing, the stent is dried at 50° C. for 1-24 hours.

Critical factors for the optimization of the above coating steps may include the viscosity of the polymer solution, the thickness of the coating layers, and drying temperature. First, the viscosity of the polymer solution is maintained within a range of 0.5-100 cps. If the viscosity is more than 100 cps, ultrasonic spraying of the polymer solution will become difficult. Second, the thickness of the coating layers needs to be maintained at a suitable level. This is because coating layers with a small thickness rapidly release the components of therapeutic agents, and coating layers with a large thickness slowly release the therapeutic agent components and has the risk of leaving the drug non-released. Thus, the preferred thickness of the coating layers is 1-30 μm. Particularly, the solvent selected for use in the coating steps should have a property allowing the uniform dispersion of the drug throughout the solvent, and preferred examples thereof include solvents with high partial vapor pressure, such as tetrahydrofuran (THF), acetone, dimethyl sulfoxide(DMSO), N-methylpyrollidone(NMP) and dichloromethane (DCM).

Figure 3:
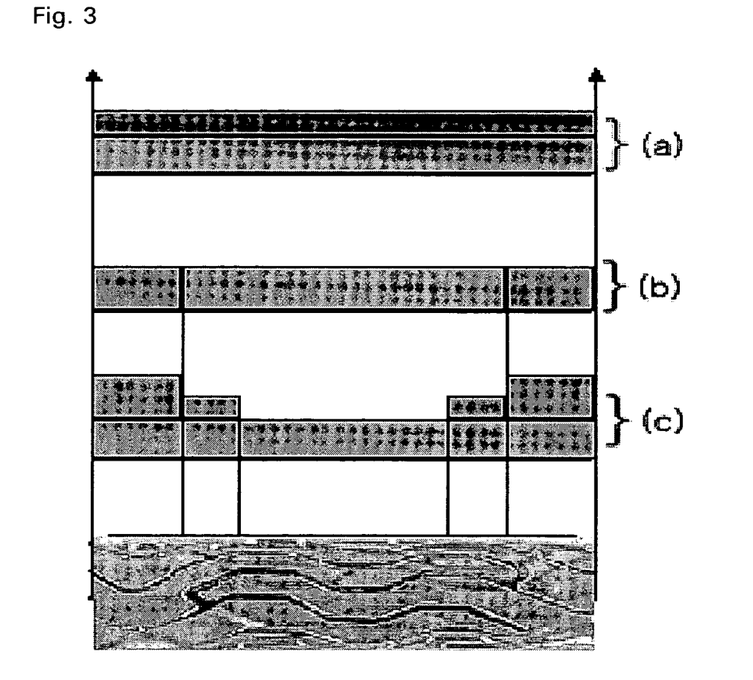
FIG. 3 is a schematic diagram showing design conditions for preventing the interaction between dissimilar drugs.

As shown in FIG. 3, a design for the three-stage separation of the two different drugs(a), a design for the separation of regions of the two different drugs(b), and a design for the uniform distribution of the two different drugs(c), can be considered to prevent the interaction between the dissimilar drugs. In multilayer-coated stent for controlled drug release according to the present invention, however, the design for the uniform distribution of the two different drugs is used to prevent the interaction between the dissimilar drugs.

Hereinafter, the present invention will be described in more detail by examples. It is to be understood, however, that these examples are not construed to limit the scope of the present invention.

EXAMPLE 1

A stent support is washed with a mixed solvent of ethanol and distilled water to remove impurities from the surface of the stent support, and dried in a vacuum oven at 50-70° C. and less than 0.1 mTorr for 12-24 hours.

A solution of 3% (w/v) polystyrene-ethylene-butylene copolymer in 150 ml of organic solvent tetrahydrofuran (THF) is spray-coated on the stent support and dried in a vacuum oven at 50-70° C. and 0.01 mTorr for 24 hours, thus forming a first base layer.

To prepare a second coating solution, 5 mg of an aqueous polyvinyl alcohol (PVA) dispersion is mixed with 150 ml of a mixed solvent of tetrahydrofuran and acetone. To the mixture, 3 mg of Cilostazol® powder (manufactured by Yuhan Chemical Inc.) is added, and stirred at room temperature for 6 hours. The solution is sprayed on the first base layer with an ultrasonic spray coating system at a power level of 0.5-1.5 watts and a flow rate of 0.05-10 ml/min. The resulting stent having the second coating layer formed thereon is vacuum dried at 85° C. for 5 hours.

To prepare a third coating solution, 3 mg of polyethylene-vinylacetate is mixed with 100 ml of tetrahydrofuran. To the mixture, 0.5 mg of Paclitaxel® powder (manufactured by Samyang Genex Corp.) is added, and stirred at room temperature for 12 hours. The third coating solution is sprayed on the second coating layer with an ultrasonic spray coating system at a power level of 0.7-1.5 watts and a flow rate of 0.10-10 ml/min. The resulting stent having the third coating layer formed thereon is dried under vacuum at 115° C. for 24 hours. This gives the multilayer-coated stent for controlled drug release.

Figure 4A:
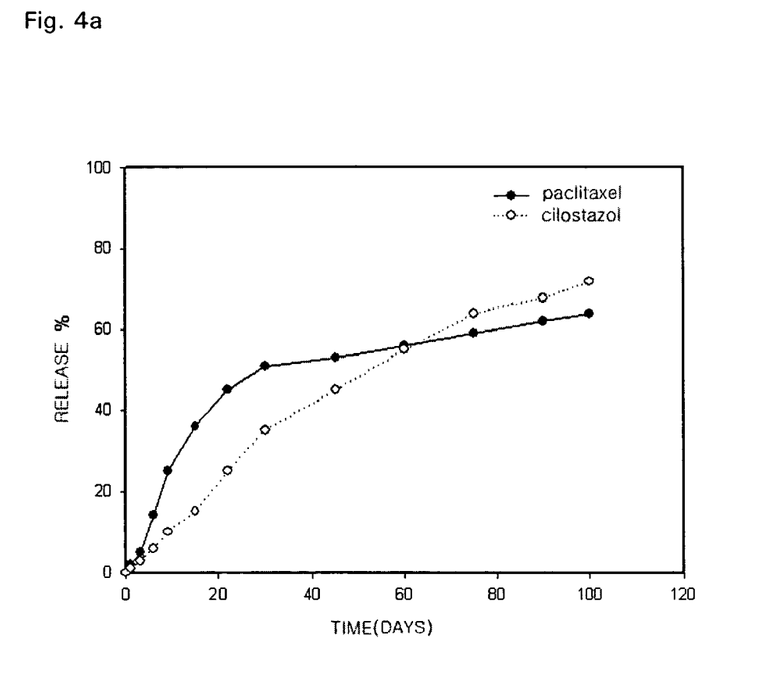
FIG. 4a shows the drug release curve of a multilayer-coated stent manufactured in Example 1.

The release effect of the multilayer-coated stent on the drugs is shown as FIG. 4a. It shows that the release rate can be well controlled.

EXAMPLE 2

A stent support is washed with a mixed solvent of ethanol and distilled water to remove impurities from the surface of the stent support, and dried in a vacuum oven at 50-70° C. and less than 0.1 mTorr for 12-24 hours.

10% (w/v) polystyrene-ethylene-butylene copolymer is added to 100 ml of organic solvent tetrahydrofuran (THF) to prepare a solution. The solution is continuously stirred at 800 rpm for 12 hours. The stirred solution is sprayed on the stent support with an ultrasonic spray coating system at a powder level of 0.5-1.6 watts and a flow rate of 0.01-10 ml/min. The coated stent is vacuum dried at 80° C. and 0.01 mTorr for 12 hours to form a first base layer.

To prepare a second coating solution, 5 mg of an aqueous polyvinyl alcohol (PVA) dispersion is mixed with 150 ml of a mixed solvent of tetrahydrofuran and acetone. To the mixture, 3 mg of Cilostazol® powder (manufactured by Yuhan Chemical Inc.) is added, and stirred at room temperature for 6 hours. The stirred solution is sprayed on the first base layer with an ultrasonic spray coating system at a power level of 0.5-1.5 watts and a flow rate of 0.05-10 ml/min. The resulting stent having the second coating layer formed thereon is dried under vacuum at 85° C. for 5 hours.

To prepare a third coating solution, 5 mg of an aqueous poly(vinyl alcohol) (PVA) dispersion and 0.5 mg of polyvinyl pyrrolidone (PVP) are added to 100 ml of tetrahydrofuran. To the mixture, 0.2 mg of Paclitaxel® powder (manufactured by Samyang Genex Corp.) is added and dissolved. The third coating solution is sprayed on the second coating layer with an ultrasonic spray coating system at a power level of 0.5-1.2 watts and a flow rate of 0.10-10 ml/min. The resulting stent having the third coating layer formed thereon is dried under vacuum at 100° C. for 12 hours.

Figure 4B:
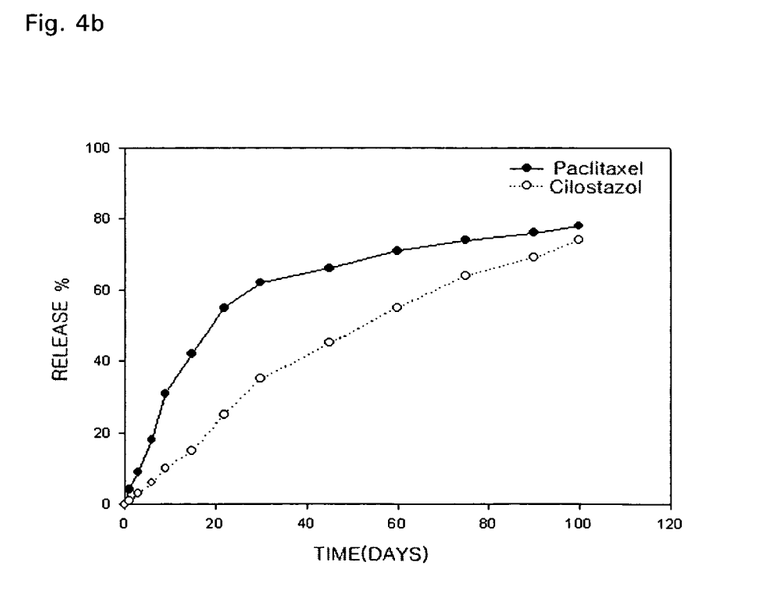
FIG. 4b shows the drug release curve of a multilayer-coated stent manufactured in Example 2.

The release effect of the multilayer-coated stent on the drugs is shown as FIG. 4b. It shows that a rapid release of therapeutic agents can be avoided and then the release rate can be well controlled.

EXAMPLE 3

A stent support is washed with a mixed solvent of ethanol and distilled water to remove impurities from the surface of the stent support, and dried in a vacuum oven at 50-70° C. and less than 0.1 mTorr for 12-24 hours.

A solution of 3 mg of 2% (w/v) polystyrene-ethylene-butylene copolymer in 150 ml of organic solvent toluene is spray coated on the stent support, and the coated stent is vacuum dried in 0.01 mTorr for 24 hours to form a first base layer.

To prepare a second coating solution, 2 mg of cellulose acetate butyrate (CAB) is mixed with 150 ml of dimethyl sulfoxide (DMSO). To the mixture, 3 mg of Cilostazol® (manufactured by Yuhan Chemical Inc.) is added, and stirred at 500 rpm for 24 hours. The stirred solution is sprayed on the first base layer with an ultrasonic spray coating system at a power level of 0.5-1.5 watts and a flow rate of 0.02-10 ml/min. The resulting stent having the second coating layer formed thereon is vacuum dried at 120° C. and 0.1 Torr for 12 hours.

To prepare a third coating solution, 5 mg of polyethylene-vinylacetate and 1 mg of polyvinyl pyrrolidone (PVP) an aqueous poly(vinyl alcohol) (PVA) are added to 150 ml of organic solvent dichloromethane (DCM). To the mixture, 0.5 mg of Paclitaxel® (manufactured by Samyang Genex Corp.) is added, and stirred at 500 rpm for 24 hours. The third coating solution is sprayed on the second coating layer with an ultrasonic spray coating system at a power level of 0.5-1.5 watts and a flow rate of 0.10-10 ml/min. The resulting stent having the third coating layer formed thereon is dried under vacuum at 100° C. for 12 hours.

Figure 4C:
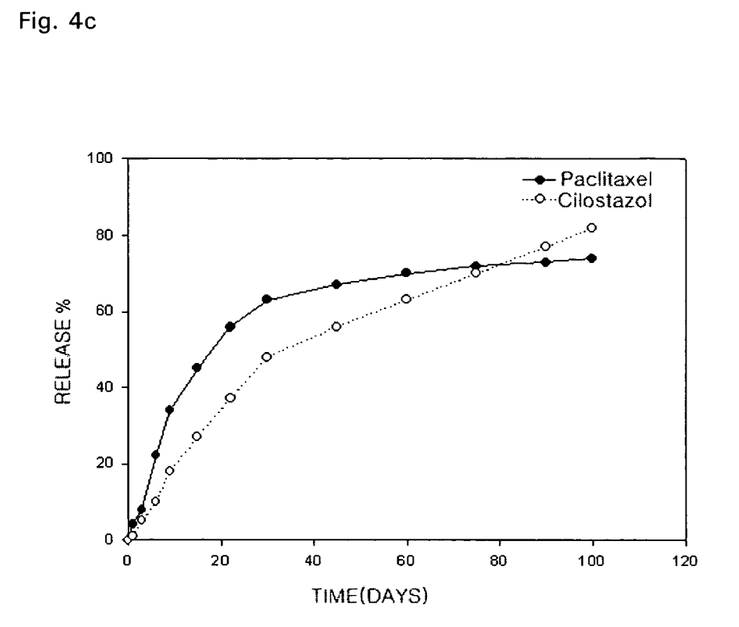
FIG. 4c shows the drug release curve of a multilayer-coated stent manufactured in Example 3.

The release effect of the multilayer-coated stent on the drugs is shown as FIG. 4c. It shows that the drugs in multilayer-coated stent will be differently released by particle dissolution or diffusion when nonbioerodable matrices are used.

EXAMPLE 4

A stent support is washed with a mixed solvent of ethanol and distilled water to remove impurities from the surface of the stent support, and dried in a vacuum oven at 50-70° C. and less than 0.1 mTorr for 12-24 hours.

A solution of 3 mg of 2% (w/v) polystyrene-ethylene-butylene copolymer in 150 ml of organic solvent toluene is spray coated on the stent support, and the coated stent is vacuum dried in 0.01 mTorr for 24 hours to form a first base layer.

To prepare a second coating solution, 2 mg of cellulose acetate butyrate (CAB) and 1 mg of Poly(D,L-lactide-co-glycolide) are mixed with 150 ml of N-methylpyrrollidone (NMP). To the mixture, 3 mg of Cilostazol® (manufactured by Yuhan Chemical Inc.) is added, and stirred at 500 rpm for 24 hours. The stirred solution is sprayed on the first base layer with an ultrasonic spray coating system at a power level of 0.9-1.5 watts and a flow rate of 0.02-10 ml/min. The resulting stent having the second coating layer formed thereon is vacuum dried at 150° C. and 0.1 Torr for 12 hours.

To prepare a third coating solution, 5 mg of polyethylene-vinylacetate and 1 mg of Poly(D,L-lactide-co-glycolide) are added to 150 ml of organic solvent N-methylpyrrolidone (NMP). To the mixture, 0.5 mg of Paclitaxel® (manufactured by Samyang Genex Corp.) is added, and stirred at 500 rpm for 24 hours. The third coating solution is sprayed on the second coating layer with an ultrasonic spray coating system at a power level of 0.9-1.5 watts and a flow rate of 0.10-10 ml/min. The resulting stent having the third coating layer formed thereon is dried under vacuum at 150° C. for 12 hours.

Figure 4D:
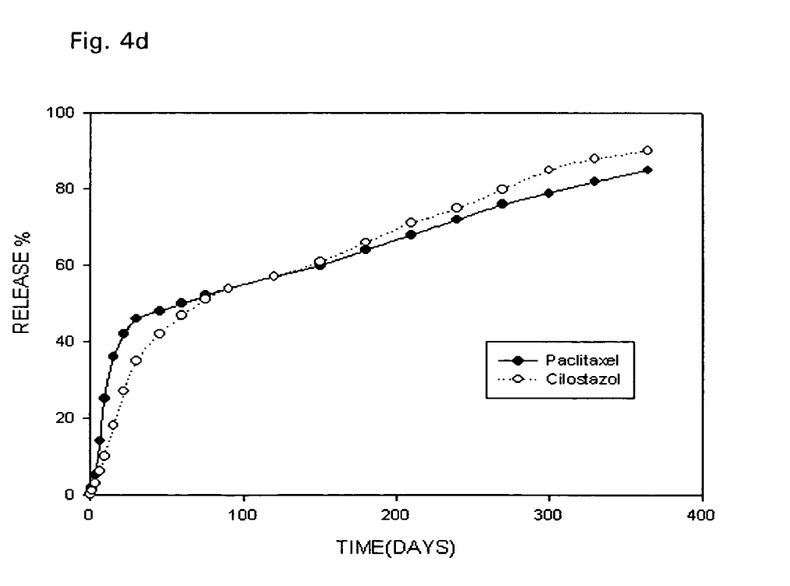
FIG. 4d shows the drug release curve of a multilayer-coated stent manufactured in Example 4.

The release effect of the multilayer-coated stent on the drugs is shown as FIG. 4d. It shows that the release kinetics of different drugs in the different coating matrix can provide the long-term sustained delivery of a medicating composition and the object of the long-term drug release can be achieved.

TEST EXAMPLE 1

In order to evaluate performance to control the release of Paclitaxel among the drugs contained in the multilayer structure of the inventive stent, 0.2 mg of each of three mixed solutions corresponding to the mixed solutions applied to the stents of Examples 1-3 is prepared in the same manner as in Examples 1-3, and then, developed on the surface of each of glass plates. Then, the glass plates are placed in an oven and dried under vacuum at 120° C. for 12 hours. The glass plates are taken out from the oven and cooled to room temperature. For the measurement of drug release, the glass plates are individually placed in 20 ml of phosphate buffered solution (pH 7.4; 37° C.). The sample is collected every day and the entire release medium is replaced with a fresh medium at each sampling point. The collected sample is filtered through 0.45 µm-sized filter paper. The drug (Paclitaxel) released from the medium is measured with high performance liquid chromatography (HPLC).

Measurement results for the mixed solutions corresponding to Examples 1-3 are shown in FIGS. 4a, 4b, 4c and 4d.

TEST EXAMPLE 2

In order to evaluate performance to control the release of Cilostazol among the drugs contained in the multilayer structure of the inventive stent, 0.2 mg of each of three mixed solutions corresponding to the mixed solutions applied to the stents of Examples 1-3 is prepared in the same manner as in Examples 1-3, and then, developed on the surface of each of glass plates. Then, the glass plates are placed in an oven and dried under vacuum at 120° C. for 12 hours. The glass plates are taken out from the oven and cooled to room temperature. For the measurement of drug release, the glass plates are individually placed in 20 ml of phosphate buffered solution (pH 7.4; 37° C.). The sample is collected every day and the entire release medium is replaced with a fresh medium at each sampling point. The collected sample is filtered through 0.45 μm-sized filter paper. The drug (Cilostazol) released from the medium is measured with high performance liquid chromatography (HPLC). In the test, Cilostazol is used in the form of a Cilostazol standard solution (200 μg/ml) made by weighing 40 mg of Cilostazol and adding acetonitrile to the drug to a final volume of 200 ml.

Measurement results for the mixed solutions corresponding to Examples 1-3 are shown in FIGS. 4a, 4b, 4c and 4d.

As described above, the multilayer-coated stent for controlled drug release according to the present invention can deliver a broad range of therapeutic substances for a long period of time and prevent the early release of the drug components in blood. Also, unlike the existing drug-coated stents, the inventive stent includes two kinds of drugs complementary to each other, but can optimize the efficacy of the drugs by differentiating the control of drug release according to time.

What is claimed is:

1. A multilayer-coated stent for controlled drug release, comprising:
   a first base layer formed on a stent support and made of poly(ethylene-co-vinylacetate) or polystyrene-ethylene-butylene rubber polymer;
   a second coating layer formed on the first base layer and made of a biocompatible polymer and a drug component; and
   a third coating layer formed on the second coating layer and made of a biocompatible polymer and a drug component different from the drug component of the second coating layer,
   wherein the stent support comprises a plurality of micropores.

2. The stent of claim 1, wherein the stent support is made of a biocompatible metal selected from the group consisting of stainless steel, cobalt-chrome alloy, tantalum, nitinol and gold.

3. The stent of claim 1, wherein the biocompatible polymer of the second coating layer and the third coating layer is selected from the group consisting of polyvinyl alcohol, polyethylene glycol, polylactide, polyglycolide, polylactide copolymer, polyethylene oxide, polydioxanone, polycaprolactone, polyphosphagen, polyanhydride, polyamino acid, cellulose acetate butyrate, polyethylene-vinylacetate, cellulose triacetate, polyacrylate, polyacrylamide, polyurethane, polysiloxane, polyvinylpyrrolidone (PVP), and copolymers thereof.

4. The stent of claim 1, wherein the drug component of the second coating layer is selected from the group consisting of an antiplatelet drug including cilostazol, an antithrombotic agent including probucol, an antiproliferative agent, a growth factor, an antioxidant, and a radioactive compound; and
   the drug component of the third coating layer is selected from the group consisting of taxol, a derivative of taxol, colchicine, lovastatin, trapidyl, hirudin, ticlopidine, a vascular endothelial growth factor, a transforming growth factor-beta, an insulin-like growth factor, a platelet-derived growth factor, and a fibroblast growth factor.

5. The stent of claim 1, wherein the drug component of the second coating layer is cilostazol, and the drug component of the third coating layer is paclitaxel.

6. The stent of claim 1, wherein the drug of the second coating layer and the drug of the third coating layer are uniformly distributed.

7. The stent of claim 1, wherein the entire thickness of the first base layer, the second coating layer and t he third coating layer is 1-30 μm.

8. A multilayer-coated stent for controlled drug release, comprising:
   a first base layer formed on a stent support and made of polystyrene-ethylene-butylene rubber polymer;
   a second coating layer formed on the first base layer and made of a biocompatible polymer and a drug component selected from the group consisting of an antiplatelet drug including cilostazol, an antithrombotic agent including probucol, an antiproliferative agent, a growth factor, an antioxidant, and a radioactive compound; and
   a third coating layer formed on the second coating layer and made of a biocompatible polymer and a drug component different from the drug component of the second coating layer, said drug component of the third coating layer being selected from the group consisting of taxol, a derivative of taxol, colchicine, lovastatin, trapidyl, hirudin, ticlopidine, a vascular endothelial growth factor, a transforming growth factor-beta, an insulin-like growth factor, a platelet-derived growth factor, and a fibroblast growth factor,
   wherein the stent support comprises a plurality of micropores.

9. The stent of claim 8, wherein the stent support is made of a biocompatible metal selected from the group consisting of stainless steel, cobalt-chrome alloy, tantalum, nitinol and gold.

10. The stent of claim 8, wherein the biocompatible polymer of the second coating layer and the third coating layer is selected from the group consisting of polyvinyl alcohol, polyethylene glycol, polylactide, polyglycolide, polylactide copolymer, polyethylene oxide, polydioxanone, polycaprolactone, polyphosphagen, polyanhydride, polyamino acid, cellulose acetate butyrate, polyethylene-vinyl acetate, cellulose triacetate, polyacrylate, polyacrylamide, polyurethane, polysiloxane, polyvinylpyrrolidone (PVP), and copolymers thereof.

11. The stent of claim 8, wherein the entire thickness of the first base layer, the second coating layer and the third coating layer is 1-30 μm.

12. The stent of claim 1, wherein the ratio of weight of the biocompatible polymer to the drug component in the second coating layer is 1:1-10:1.

13. The stent of claim 1, wherein the ratio of weight of the biocompatible polymer to the drug component in the third coating layer is 1:5-10:1.

14. A multilayer-coated stent for controlled drug release, comprising:
   a first base layer formed on a stent support and made of polystyrene-ethylene-butylene rubber polymer;
   a second coating layer formed on the first base layer and made of a biocompatible polymer and a drug component; and
   a third coating layer formed on the second coating layer and made of a biocompatible polymer and a drug component different from the drug component of the second coating layer,
   wherein the ratio of weight of the biocompatible polymer to the drug component in the second coating layer is 1:1-10:1, and
   wherein the ratio of weight of the biocompatible polymer to the drug component in the third coating layer is 1:5-10:1.

15. A multilayer-coated stent for controlled drug release, comprising:
- a first base layer formed on a stent support and made of polystyrene-ethylene-butylene rubber polymer;
- a second coating layer formed on the first base layer and made of a biocompatible polymer and a drug component selected from the group consisting of an antiplatelet drug including cilostazol, an antithrombotic agent including probucol, an antiproliferative agent, a growth factor, an antioxidant, and a radioactive compound; and
- a third coating layer formed on the second coating layer and made of a biocompatible polymer and a drug component different from the drug component of the second coating layer, said drug component of the third coating layer being selected from the group consisting of taxol, derivative of taxol, colchicine, lovastatin, trapidyl, hirudin, ticlopidine, a vascular endothelial growth factor, a transforming growth factor-beta, an insulin-like growth factor, a platelet-derived growth factor, and a fibroblast growth factor,
- wherein the ratio of weight of the biocompatible polymer to the drug component in the second coating layer is 1:1-10:1, and
- wherein the ratio of weight of the biocompatible polymer to the drug component in the third coating layer is 1:5-10:1.

* * * * *